(12) United States Patent
Hagemeyer et al.

(10) Patent No.: US 8,480,998 B2
(45) Date of Patent: Jul. 9, 2013

(54) METHOD FOR THE PRODUCTION OF NANOCRYSTALLINE BISMUTH-MOLYBDENUM MIXED OXIDE

(75) Inventors: Alfred Hagemeyer, Bad Aibling (DE); Oliver Wegner, Heufeldmühle (DE); Silvia Neumann, Grosskarolinenfeld (DE); Hans-Jörg Wölk, Rosenheim (DE)

(73) Assignee: Sued-Chemie IP GmbH & Co. KG, Munich (DE)

( * ) Notice: Subject to any disclaimer, the term of this patent is extended or adjusted under 35 U.S.C. 154(b) by 238 days.

(21) Appl. No.: 12/935,710

(22) PCT Filed: Apr. 3, 2009

(86) PCT No.: PCT/EP2009/002475
§ 371 (c)(1), (2), (4) Date: Dec. 13, 2010

(87) PCT Pub. No.: WO2009/121625
PCT Pub. Date: Oct. 8, 2009

(65) Prior Publication Data
US 2011/0092734 A1    Apr. 21, 2011

(30) Foreign Application Priority Data
Apr. 4, 2008    (DE) .......................... 10 2008 017 308

(51) Int. Cl.
*C01G 49/00*    (2006.01)
(52) U.S. Cl.
USPC ........................................ 423/594.7; 502/311
(58) Field of Classification Search
USPC ........................................ 423/594.7; 502/311
See application file for complete search history.

(56) References Cited

U.S. PATENT DOCUMENTS

| 6,652,967 | B2 * | 11/2003 | Yadav et al. | 428/403 |
| 2004/0077481 | A1 * | 4/2004 | Remke et al. | 501/94 |
| 2007/0238904 | A1 | 10/2007 | Liang et al. | |
| 2008/0247931 | A1 * | 10/2008 | Domesle et al. | 423/263 |
| 2009/0030230 | A1 | 1/2009 | Fischer et al. | |
| 2009/0325794 | A1 | 12/2009 | Wölk et al. | |
| 2010/0015446 | A1 | 1/2010 | Wölk | |

FOREIGN PATENT DOCUMENTS

| DE | 101 09 892 A1 | 9/2002 |
| DE | 10 2006 015 710 A1 | 4/2007 |
| DE | 10 2006 032 452 A1 | 1/2008 |
| EP | 1 767 267 A2 | 3/2007 |
| FR | 2 826 959 | 1/2003 |
| KR | 1999-0077024 | 10/1999 |
| WO | WO 2007/042369 A1 | 4/2007 |
| WO | WO 2008/006565 A1 | 1/2008 |
| WO | WO 2008/028681 A2 | 3/2008 |

OTHER PUBLICATIONS

G. A. Zenikovets et al., "The structural genesis of a complex MoVW)$_x$O$_{14}$ oxide during thermal treatments and its redox behavior at elevated temperatures," Materials Chemistry and Physics, 103 (2007), 295-304.
International Search Report of PCT/EP2009/002475, dated Jul. 20, 2009.

* cited by examiner

*Primary Examiner* — Steven Bos
(74) *Attorney, Agent, or Firm* — RatnerPrestia

(57) ABSTRACT

A method for the production of a nanocrystalline bismuth-molybdenum mixed oxide, the use of the bismuth-molybdenum mixed oxide as catalyst for chemical conversions, in particular for a conversion of propylene to acrolein and/or acrylic acid or of isobutylene to methacrolein and/or methacrylic acid, as well as a catalyst that contains the bismuth-molybdenum mixed oxide.

6 Claims, 4 Drawing Sheets

METHOD FOR THE PRODUCTION OF NANOCRYSTALLINE BISMUTH-MOLYBDENUM MIXED OXIDE

CROSS REFERENCE TO RELATED APPLICATIONS

This is a National Phase application of PCT application number PCT/EP2009/002475, filed Apr. 3, 2009, which claims priority benefit of German application number DE 10 2008 017 308.8, filed Apr. 4, 2008, the content of such applications being incorporated herein by reference.

FIELD OF THE INVENTION

The invention relates to a method for the production of a nanocrystalline bismuth-molybdenum mixed oxide, the use of the bismuth-molybdenum mixed oxide as catalyst for chemical conversions as well as a catalyst which contains the bismuth-molybdenum mixed oxide.

BACKGROUND OF THE INVENTION

Until now, bismuth-molybdenum mixed oxides have been obtained in the state of the art by precipitation methods, sol-gel methods or solid-state reactions.

US 2007/0238904 A1 discloses a bismuth-molybdenum mixed oxide which is obtained by precipitation and subsequent calcining. The bismuth-molybdenum mixed oxide is suitable as catalyst for the conversion of propylene or isobutylene to acrolein or methacrolein.

WO 2008/028681 and DE 10 2006 032 452 A1 disclose a method for the production of nanocrystalline metal oxides or mixed metal oxides. There is no indication in these documents that special nanocrystalline bismuth-molybdenum mixed oxides which are particularly suitable as catalyst for the conversion of for example propylene to acrolein can be produced with the method.

A crystalline molybdenum mixed oxide and thus also a bismuth-molybdenum mixed oxide can be obtained only with difficulty via conventional methods. Thus, G. A. Zenkovets et al., "The structural genesis of a complex $(MoVW)_5O_{14}$ oxide during thermal treatments and its redox behaviour at elevated temperatures", Materials Chemistry and Physics, 103 (2007), 295-304, disclose that a molybdenum mixed oxide obtained via precipitation and spray drying has an amorphous structure. This mixed oxide is present in the form of large aggregates approximately 5 μm in size. A partially nanocrystalline structure forms inside the aggregates due to subsequent calcining. A pure crystalline phase with crystallites more than 1000 nm in size forms only after prolonged thermal treatment at approximately 440° C. The production of a nanocrystalline molybdenum mixed oxide can thus be accomplished only with difficulty, in particular with regard to the production of small crystallites.

A disadvantage of the lead-molybdenum mixed oxides of the state of the art is thus in particular that a uniform particle size of the molybdenum mixed oxides cannot be obtained and a control of the crystallization, in particular with regard to the crystallite size, is not possible. The BET surface area of the molybdenum mixed oxides of the state of the art is likewise mostly too small. A small particle size with as large as possible a BET surface area is desired, in particular for catalytic uses.

DESCRIPTION OF THE INVENTION

An object of the present invention was thus the provision of a method with which a nanocrystalline bismuth-molybdenum mixed oxide can be obtained which, as catalyst in catalytic conversions, has an increased activity and selectivity for the desired end product.

An object is achieved by a method for the production of a nanocrystalline bismuth-molybdenum mixed oxide, comprising the steps of
  a) the introduction of a solution, suspension or slurry, containing a molybdenum starting compound and a bismuth starting compound, into a reaction chamber by means of a carrier fluid,
  b) a thermal treatment of the solution, suspension or slurry which contains the molybdenum starting compound and the bismuth starting compound in a treatment zone by means of a pulsating flow at a temperature of from 200 to 700° C.,
  c) the formation of a nanocrystalline bismuth-molybdenum mixed oxide,
  d) the discharge of the nanocrystalline bismuth-molybdenum mixed oxide obtained in steps b) and c) from the reactor.

It was surprisingly found that a uniform particle size of the obtained bismuth-molybdenum mixed oxide can be obtained by the method according to aspects of the invention and a control of the crystallization, in particular with regard to the crystallite size, is achieved. The BET surface area of the thus-obtained bismuth-molybdenum mixed oxide was likewise able to be increased compared with the state of the art.

The bismuth-molybdenum mixed oxide obtained according to aspects of the invention is characterized by a crystallite size in the range of from 10 nm to 1000 nm, in particular from 10 nm to 750 nm, preferably 10 nm to 500 nm and more preferably 10 nm to 300 nm and further preferably 10 nm to 100 nm, in particular 10 nm to 30 nm.

The catalytic activity of a catalyst, containing the bismuth-molybdenum mixed oxide according to aspects of the invention, in particular in the case of a conversion of propylene to acrolein, was able to be increased by up to 10%, compared with catalysts which contain conventionally produced bismuth-molybdenum mixed oxides.

Through the increased activity and selectivity of such a catalyst according to aspects of the invention, a production of acrolein from propylene that is clearly improved compared with the state of the art is possible. A conversion of isobutylene to methacrolein or analogous compounds is also possible with this catalyst. This catalyst also displays in particular a very good activity in the case of a direct conversion of propylene or isobutylene to acrylic acid or methacrylic acid, wherein the conversion can preferably take place in one step according to aspects of the invention.

Preferably a molybdate, particularly preferably ammonium heptamolybdate tetrahydrate, is used as molybdenum starting compound. However, it is clear to a person skilled in the art in this field that other molybdates and molybdenum compounds known in the state of the art can also be used.

A bismuth salt, such as bismuth chloride, bismuth sulphate, bismuth acetate, bismuth oxide, particularly preferably bismuth nitrate, is preferably used as bismuth starting compound.

The molybdenum starting compound and the bismuth starting compound are preferably used together as solution, suspension or slurry. It is most preferred if the starting compounds are present as solution. In order to obtain an optimum solution, in particular in the case of poorly soluble starting compounds, the solution can additionally be heated, for example to >50° C.

In a particularly preferred embodiment, still further metal-containing starting compounds can be present together with the molybdenum and bismuth starting compound in the solution, suspension or slurry. Metal compounds of nickel, iron and/or zinc are preferred in this connection. Co and Mn are also preferred metals. These metals are preferably used as metal salts, in particular as oxides, halides, sulphates, nitrates or acetates.

Further preferably, metal compounds or non-metal compounds, selected from Li, Na, K, Rb, Cs, Mg, Ca, Ba, Sr, Ce, Mn, Cr, V, Nb, Se, Te, Sm, Gd, La, Y, Pd, Pt, Ru, Ag, Au, Si, Al, Tl, Zr, W and/or P, can also be additionally used.

It was surprisingly found that the method can be carried out at relatively low temperatures of from 200 to 700° C., preferably 200 to 500° C., particularly preferably from 250 to 450° C., particularly preferably from 300 to 400° C. Hitherto, preferred temperatures of more than 700° C., indeed up to 1400° C., were known in the state of the art. Quite particularly surprisingly, it was also found that the crystallization process of the bismuth-molybdenum mixed oxide can be controlled in a targeted manner by the method according to aspects of the invention, in particular the size of the crystallites and the pore-size distribution of the corresponding bismuth-molybdenum mixed oxides. This can further be advantageously influenced by the residence time in the flame or by the reactor temperature. The nanocrystalline bismuth-molybdenum mixed oxide particles that form are prevented from agglomerating by the pulsating thermal treatment. Typically, the nanocrystalline particles are immediately transferred by the stream of hot gas into a colder zone, wherein some of the bismuth-molybdenum mixed oxide crystallites are obtained with diameters of less than 20 nm.

In the case of the thus-obtainable bismuth-molybdenum mixed oxide crystallites, this leads to clearly increased BET surface areas of $>1$ $m^2/g$, particularly preferably 2 to 50 $m^2/g$ and particularly preferably 5 to 35 $m^2/g$. The BET surface area is determined according to DIN 66131 and 66132 (using the Brunauer, Emmett and Teller method).

In the method according to aspects of the invention, suspensions can be calcined within a very short period, typically within a few milliseconds, at comparatively lower temperatures than are usual with methods of the state of the art, without additional filtration and/or drying steps or without the addition of additional solvents. The bismuth-molybdenum mixed oxide nanocrystallites that form have significantly increased BET surface areas. Thus, in a further embodiment of the present invention, a catalyst containing the bismuth-molybdenum mixed oxide according to aspects of the invention ("bismuth-molybdenum mixed oxide catalyst") with increased reactivity, improved rate of conversion and improved selectivity, in particular with regard to a conversion of propylene to acrolein and/or acrylic acid or isobutylene to methacrolein and/or methacrylic acid can be provided.

The nearly identical residence time of every bismuth-molybdenum mixed oxide particle in the homogeneous temperature field created by the method results in an extremely homogeneous end product with narrow monomodal particle distribution. A device for carrying out the method according to aspects of the invention in the production of such monomodal nanocrystalline metal oxide powders is known for example from DE 101 09 892 A1. Unlike the device described there and the method disclosed there, the present method does not, however, require an upstream evaporation step in which the starting material, i.e. the molybdenum starting compound, is heated to an evaporation temperature.

The molybdenum starting compound, the bismuth starting compound and the further starting compounds from which the bismuth-molybdenum mixed oxide according to aspects of the invention is produced are inserted directly via a carrier fluid, in particular a carrier gas, preferably an inert carrier gas, such as for example nitrogen, etc., into so-called reaction chambers, i.e. into the combustion chamber. Attached exhaust side to the reaction chamber is a resonance tube with a flow cross-section which is clearly reduced compared with the reaction chamber. The floor of the combustion chamber is equipped with several valves for the entry of the combustion air into the combustion chamber. The aerodynamic valves are fluidically and acoustically matched with the combustion chamber and the resonance tube geometry such that the pressure waves, created in the combustion chamber, of the homogeneous "flameless" temperature field spread pulsating predominantly in the resonance tube. A so-called Helmholtz resonator forms with pulsating flow with a pulsation frequency of between 3 and 150 Hz, preferably 5 to 110 Hz.

Material is typically fed into the reaction chamber either with an injector or with a suitable two-component nozzle, three-component nozzle or in a Schenk dispenser.

Preferably, the molybdenum starting compound, the bismuth starting compound and optionally the further starting compounds are introduced into the reaction chamber in atomized form, with the result that a fine distribution in the region of the treatment zones is guaranteed.

After the thermal treatment, the nanocrystalline bismuth-molybdenum mixed oxides that form are immediately transferred into a colder zone of the reaction chamber, if possible by means of the carrier fluid, with the result that they can be separated and discharged in the colder zone. The yield of the method according to aspects of the invention is almost 100%, as all of the product that forms can be discharged from the reactor.

Typically, the method is carried out at a pressure in the range of from normal pressure to 40 bar.

A subject of the invention is furthermore the nanocrystalline bismuth-molybdenum mixed oxide that can be obtained by the method according to aspects of the invention. It was found that the thus-obtainable nanocrystalline bismuth-molybdenum mixed oxide preferably has a crystallite size in the range of from 5 nm to 1000 nm, preferably of from 10 nm to 800 nm, quite particularly preferably 15 to 550 nm, which, as already stated above, can preferably be set by the pulsation of the thermal treatment. The particle size can be determined by methods known to a person skilled in the art, such as XRD or TEM.

Furthermore, bismuth-molybdenum oxide particles which have a BET surface area of preferably $>1$ $m^2/g$, particularly preferably 2 to 50 $m^2/g$ and quite particularly preferably 5 to 35 $m^2/g$ are obtained by the method according to aspects of the invention.

A preferred bismuth-molybdenum mixed oxide according to aspects of the invention can be described by the general formula $Mo_aBi_b(CoNi)_cFe_dKO_x$. This formula gives the active catalyst component without the carrier material. A bismuth-molybdenum mixed oxide with the formula $MoBiO_x$ is particularly preferred. A further formula for a bismuth-molybdenum mixed oxide in which still further elements are present is for example $Mo_aBi_b(CoNi)_cFe_dMn_eK_fP_gAl_hSi_iSm_jO_x$ wherein preferably a is 10-13, b is 1-2, c is 7-9, d is 1.5-2.3, e is 0.05-0.3 f is 0.02-0.1, g is 0.01-0.1, h is 270-280, i is 0.4-0.9, j is 0.05-0.15 and x is 2 or more. A particularly preferred composition within this general formula can be represented by the formula $Mo_{12}Bi_{1.5}(CoNi)_{8.0}Fe_{1.8}Mn_{0.1}K_{0.06}P_{0.04}Al_{275}Si_{0.66}Sm_{0.1}O_x$.

The molybdenum mixed oxide according to aspects of the invention is suitable in preferred developments of the present invention for use as catalytically active component of a catalyst, for example of a catalyst for the conversion of propylene to acrolein and/or acrylic acid or isobutylene to methacrolein and/or methacrylic acid. In particular, this catalyst according to aspects of the invention is also suitable for a direct conversion of propylene or isobutylene to acrylic acid or methacrylic acid, wherein the conversion can, advantageously compared with the state of the art, take place in one step.

In industry, acrolein serves as starting material for the production of acrylic acid. Large-scale industrial production usually takes place in the state of the art by a two-stage oxidation of propylene with the aid of catalysts. In the first stage, propylene is converted with air to propenal (acrolein). The oxidation of propenal to acrylic acid takes place in the second stage. The main use of acrylic acid is polymerization to superabsorbent polymers (use e.g. in nappies), acrylate esters (which are in turn used for the production of polymers) and as comonomers in the production of polymer dispersions. The water-soluble polymerisates of acrylic acid are used as finishes and thickeners as well as coatings for solid dosage forms and as ointment bases. Polyacrylic acid ethyl ester has proved its worth as copolymerization partner for the production of weather-proof elastomers.

It was surprisingly found that a single-stage synthesis of acrolein and/or acrylic acid from propylene or methacrolein and/or methacrylic acid from isobutylene can be carried out with the bismuth-molybdenum mixed oxide catalyst according to aspects of the invention.

A subject of the invention is thus also a catalyst which contains the bismuth-molybdenum mixed oxide according to aspects of the invention. The catalyst can be a supported or an unsupported catalyst.

The bismuth-molybdenum mixed oxide can be processed together with a suitable binder to an extrudate (tablets, shaped bodies, honeycomb bodies and the like). Any binder that is familiar to a person skilled in the art and appears suitable, in particular silicate materials, aluminium oxide, zirconium compounds, titanium oxide, as well as their mixtures, and materials such as e.g. cement, clay, silica/alumina, can be used as binders. Preferred binders are, among others, pseudo-boehmite as well as siliceous binders such as colloidal silicon oxide or silica sol.

The bismuth-molybdenum mixed oxide can furthermore be processed together with other components, preferably with a binder, particularly preferably with an organic binder, for example organic glues, polymers, resins or waxes, to a washcoat which can be applied to a metallic or ceramic support. Optionally, additional impregnating steps or calcining steps can take place.

Preferably, the bismuth-molybdenum mixed oxide according to aspects of the invention is present as coating on a support. A preferred support material is steatite, steatite spheres are particularly preferred. Preferably, a so-called fluidized bed coating device is used to carry out the coating.

A subject of the invention is also a method for the conversion of propylene to acrolein and/or acrylic acid or isobutylene to methacrolein and/or methacrylic acid, wherein a catalyst according to aspects of the invention, as described above, is used.

The method preferably takes place in one stage. The method is carried out by passing a mixture of propylene or isobutylene, oxygen and nitrogen at 300 to 600° C. over a bed of the catalyst. The bed can be a packed bed or a fluid bed.

The invention is described in more detail with reference to the following embodiment examples and figures, which are not to be regarded as limitative. The device used corresponds largely to the device described in DE 101 09 892 A1, with the difference that the device used for carrying out the method according to aspects of the invention had no preliminary evaporator stage.

EMBODIMENT EXAMPLES

Figure 1:
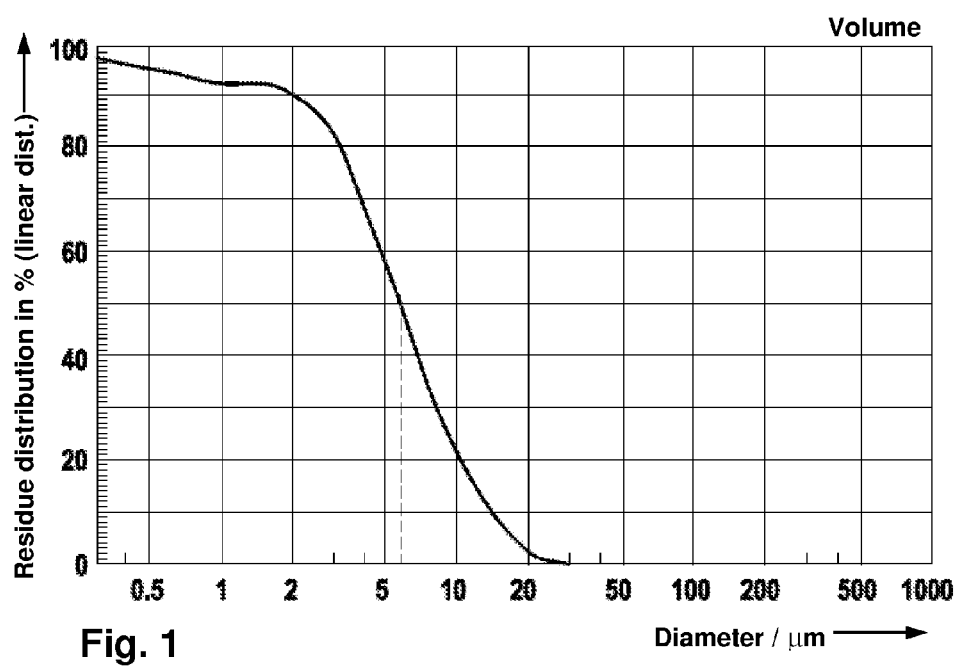
FIG. 1 shows the particle-size distribution of the suspension from Example 2.

General:

The essential advantages of the preparation with the aid of the pulsation reactor are the reduction of the overall preparation time, the small outlay (only the reactor is needed) and the fact that there is no drying and treatment of the product. The desired BET surface areas, particle sizes and also the crystallinity of the material can be varied in one step by the pulsation reactor.

Example 1

Comparison Example (According to DE 10 2006 015710 A1)

A solution I was produced by dissolving nitrates of iron, cobalt, nickel, manganese, potassium in the proportions by mass 23.2:47.26:29.28:0.0646:0.2067 in 3.5 liters of water, heating to 40° C. accompanied by stirring and adding a nitric acid solution of 0.1 mol $Sm^{3+}$ and 2 mol $HNO_3$.

For a solution II, a solution of 2118.6 g ammonium heptamolybdate in 2.7 l water was prepared at 40° C., 4.4 g phosphoric acid as well as 0.428 g Aerosil 200 (Degussa) and 14 g aluminium oxide in 1 l water were added to it.

Solution II was added slowly and accompanied by intensive stirring to solution I. In a separate vessel, a solution III, consisting of 790 g bismuth nitrate and 0.72 mol $HNO_3$, was prepared. The coprecipitate for the production of the active catalyst phase was obtained by adding this solution to the other active components.

The coprecipitate was stirred intensively for 12 hours. The obtained suspension was dried in a spray dryer with a rotary disk at a gas-entry temperature of 350° C. The quantity of air was set such that an exit temperature of 100+/−10° C. was obtained.

The obtained average particle diameter of the thus-produced powder was 55 μm. This powder was treated in a convection oven at a temperature of 445° C. for 1 hour, until a mixed oxide formed which was ground in the next step to an average particle diameter of 1 μm. The mixed oxide was sprayed as aqueous suspension through a two-component nozzle onto a ceramic spherical catalyst support and dried at 60° C. in the air flow. These were circulated in a drum to homogenize the pellets. The obtained product was heated to 540° C. for 1 hour to solidify the applied active material.

The thus-produced catalyst had the composition $(Mo_{12}Bi_{1.5}(Co+Ni)_{8.0}Fe_{1.8}Mn_{0.1}K_{0.06}P_{0.04}Al_{275}Si_{0.66}Sm_{0.1})O_x$.

Test of the Catalyst:

The catalyst of Example 1 was coated with a mixture composed of 7.5 vol.-% propylene (chemical grade), 58 vol.-% air, and inert gas (total 100 vol.-%). The total gas flow was 36.9 l/min. The temperature of the heat carrier was 365° C. The rate of conversion of the propylene was 89.5 mol-%, the product selectivity for acrolein and acrylic acid was 95.3% (see also Example 7, Table 1).

Example 2

According to Aspects of the Invention 60 l demineralized water was weighed into a 100-l vessel. This was heated to 50° C. The following substances were added to the demineralized water in succession:

| Substance | Quantity [g] | Colour of solution after addition |
|---|---|---|
| Nickel nitrate solution (Ni: 12%) | 6599.25 | green |
| Iron nitrate × 9H$_2$O | 1664.68 | green |
| Zinc nitrate × 6H$_2$O | 1202.67 | green |
| Ammonium heptamolybdate × 4H$_2$O | 4344.48 | green-yellow |

The suspension was heated to 75° C. accompanied by stirring. The suspension was cooled to 64° C. and then 3290 g Ludox® AS40 was added. The bismuth nitrate solution (2.5 l 10% nitric acid+991.04 g bismuth nitrate×5H$_2$O) was then added at a temperature of 62° C. The suspension now had a temperature of 58° C. and was stirred for 10 minutes.

The particle-size distribution of the suspension was determined: the results are to be seen in FIG. 1.

Figure 2:
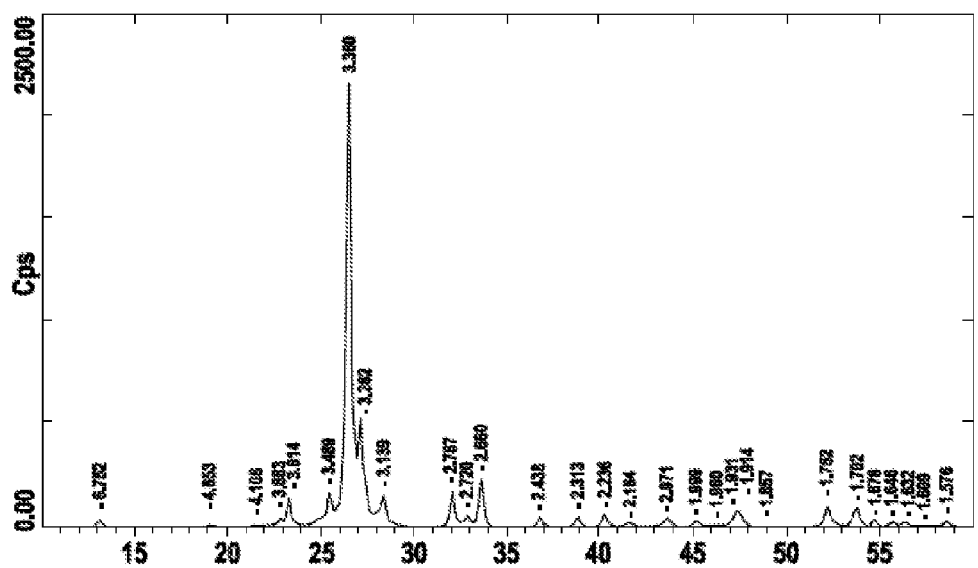
FIG. 2 shows the XRD spectrum of the bismuth-molybdenum mixed oxide according to aspects of the invention which was obtained at 450° C.

The suspension was injected into the pulsation reactor at a dispensing rate of 20 kg/h. The temperature was 450° C. The XRD spectrum of the obtained samples shows the following result:

The material produced at 450° C. in the pulsation reactor as catalyst has a BET surface area of 23 m$^2$/g and is characterized by the powder diffractogram (XRD) shown in FIG. 2.

The decomposition of the nitrate precursors as well as the formation of metal-molybdate phases such as e.g. bismuth molybdate can be seen from the XRD diffractogram.

For the coating tests described below, 1.45 kg of the material atomized at 450° C. in the pulsation reactor was produced.

Example 3

According to Aspects of the Invention 60 l demineralized water was weighed into a 100-l vessel. This was heated to 50° C. The following compounds were added to the demineralized water in succession:

| Substance | Quantity [g] | Colour of solution after addition |
|---|---|---|
| Nickel nitrate solution (Ni: 12%) | 6599.25 | green |
| Iron nitrate × 9H$_2$O | 1664.68 | green |
| Zinc nitrate × 6H$_2$O | 1202.67 | green |
| Ammonium heptamolybdate × 4H$_2$O | 4344.48 | green-yellow |

The suspension was heated to 75° C. accompanied by stirring. The suspension was cooled to 64° C. and then 3290 g Ludox® AS40 was added. The bismuth nitrate solution (2.5 l 10% nitric acid+991.04 g bismuth nitrate×5H$_2$O) was then added at a temperature of 62° C. The suspension now had a temperature of 58° C. and was stirred for 10 minutes.

Figure 3:
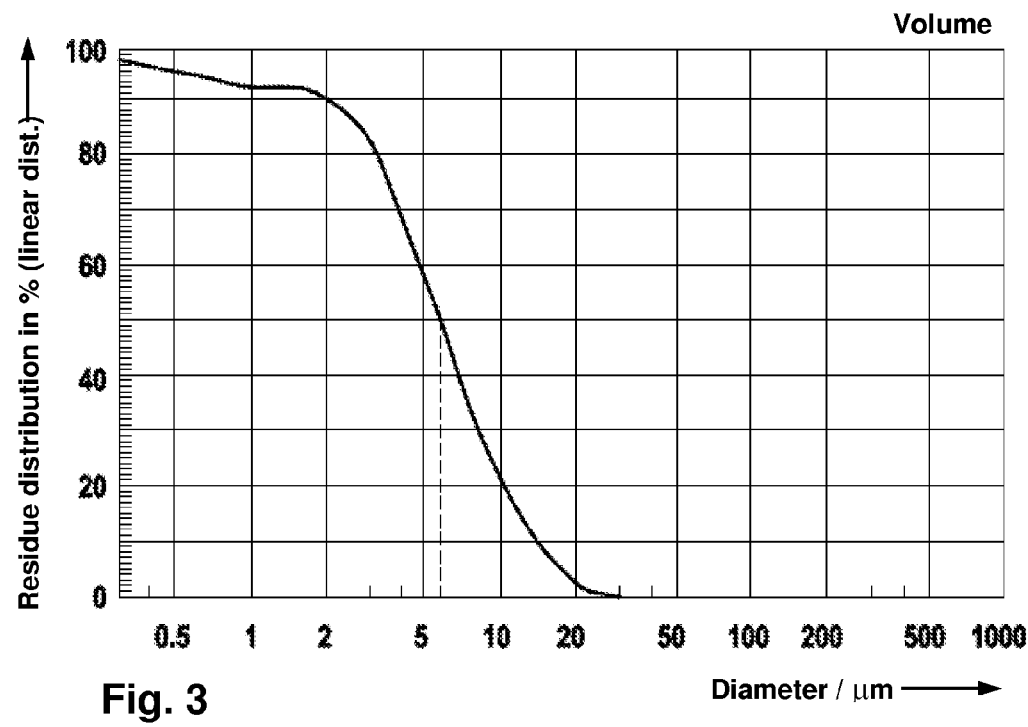
FIG. 3 shows the particle-size distribution of the suspension from Example 3.

The particle-size distribution of the suspension was determined. The results are to be found in FIG. 3.

The suspension was injected into the pulsation reactor at a dispensing rate of 20 kg/h.

Figure 4:
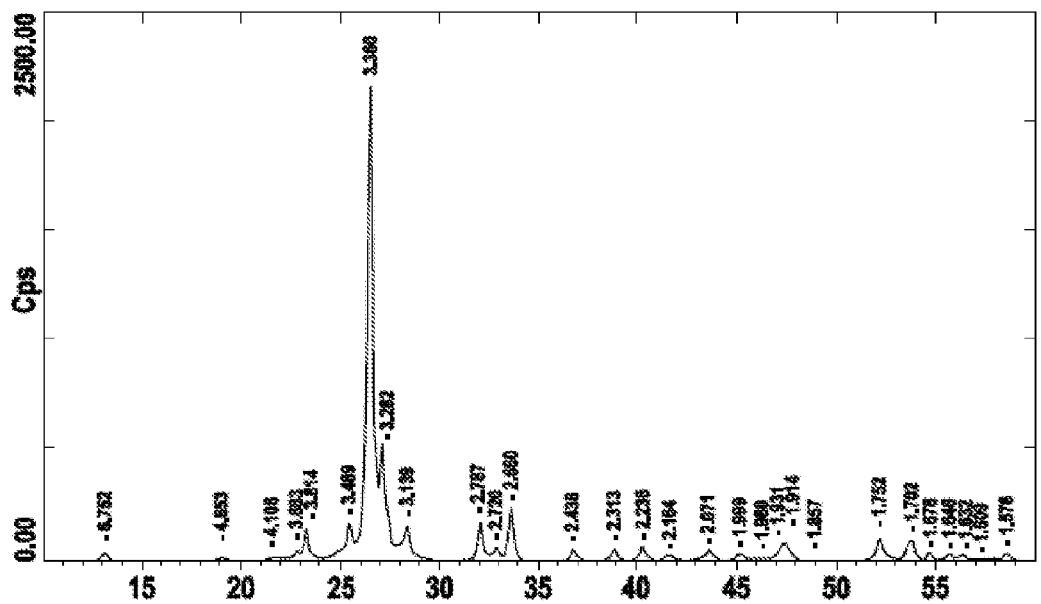
FIG. 4 shows the XRD spectrum of the bismuth-molybdenum mixed oxide according to aspects of the invention which was obtained at 500° C.

The obtained material was atomized at 500° C. in the pulsation reactor. The XRD diffractogram of the obtained samples shows the following result:

The material produced at 500° C. in the pulsation reactor has a BET surface area of 21 m$^2$/g and is characterized by the diffractogram shown in FIG. 4.

The decomposition of the nitrate precursors as well as the formation of metal-molybdate phases such as e.g. bismuth molybdate can be seen from the XRD diffractogram. Because of the Bi deficit, the main fraction of the examined catalysts consists of iron molybdate in all cases.

For the coating tests described below, 1.45 kg of the powder atomized at 500° C. in the pulsation reactor was produced.

Example 4

According to Aspects of the Invention 60 l demineralized water was weighed into a 100-l vessel. This was heated to 50° C. The following substances were added to the demineralized water in succession:

| Substance | Quantity [g] | Colour of solution after addition |
|---|---|---|
| Nickel nitrate solution (Ni: 12%) | 6599.25 | green |
| Iron nitrate × 9H$_2$O | 1664.68 | green |
| Zinc nitrate × 6H$_2$O | 1202.67 | green |
| Ammonium heptamolybdate × 4H$_2$O | 4344.48 | green-yellow |

The suspension was heated to 75° C. accompanied by stirring. The suspension was cooled to 64° C. and then 3290 g Ludox® AS40 was added. The bismuth nitrate solution (2.5 l 10% nitric acid+991.04 g bismuth nitrate×5H$_2$O) was then added at a temperature of 62° C. The suspension now had a temperature of 58° C. and was stirred for 10 minutes.

Figure 5:
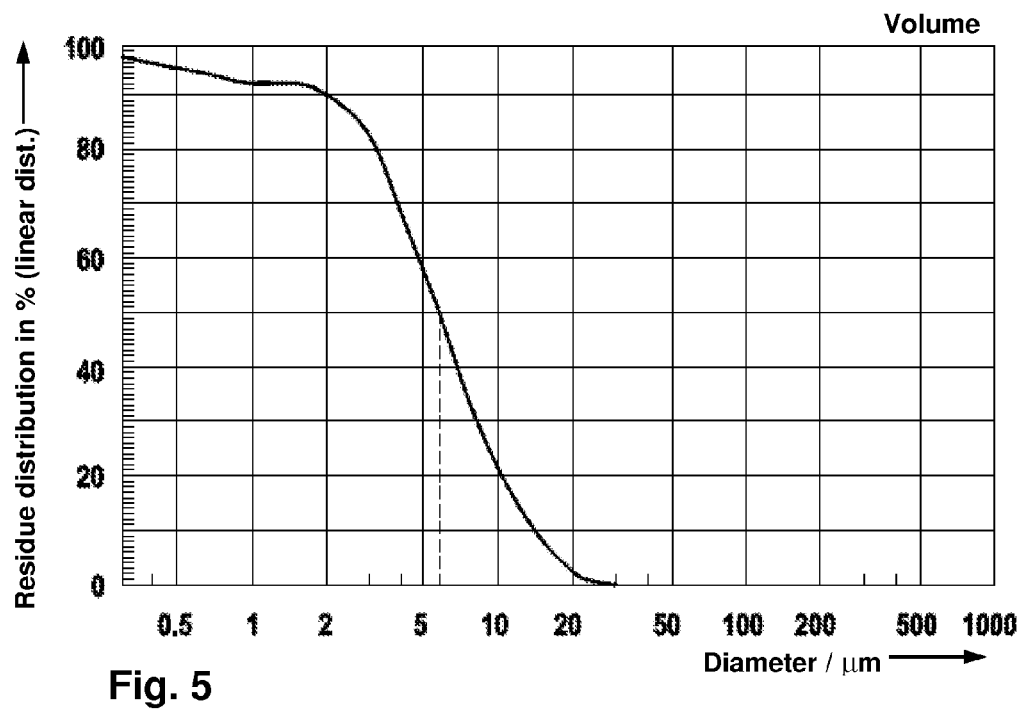
FIG. 5 shows the particle-size distribution of the suspension from Example 4.

The particle-size distribution of the suspension was determined: the results are to be found in FIG. 5.

The suspension was injected into the pulsation reactor at a dispensing rate of 20 kg/h. The obtained material was atomized at 600° C. in the pulsation reactor.

Figure 7:
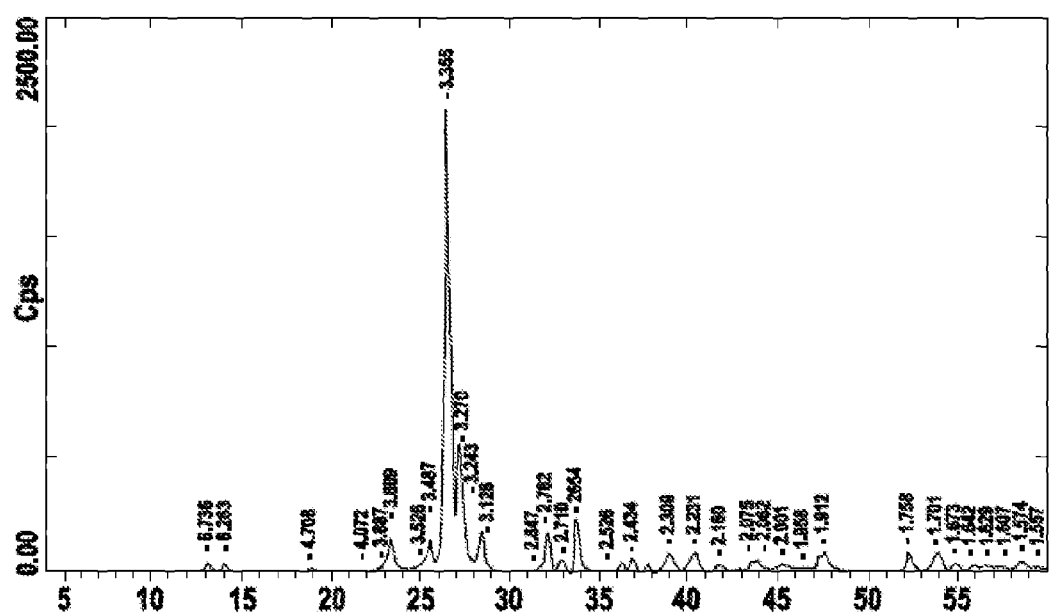
FIG. 7 shows the XRD spectrum of the bismuth-molybdenum mixed oxide according to aspects of the invention obtained at 600° C.

The material produced at 600° C. in the pulsation reactor had a BET surface area of 18 m$^2$/g and is characterized by the diffractogram represented in FIG. 7.

The decomposition of the nitrate precursors and the formation of a $BiMoO_4$ phase can be seen from the XRD diffractogram.

For the coating tests described below, 1.45 kg of the powder atomized at 600° C. in the pulsation reactor was produced.

Example 5

According to Aspects of the Invention $1^{st}$ solution: 40 l demineralized water was weighed into a 100-l vessel. This was heated to 55° C. The following substances were added to the demineralized water in succession.

| Substance | Quantity [g] | Temperature [° C.] | pH value | Colour of solution after addition |
|---|---|---|---|---|
| Iron nitrate × 9H$_2$O | 587.12 | 55 | 2.73 | orange |
| Nickel nitrate solution (Ni: 12%) | 7108.15 | 50 | 1.92 | green |
| Cobalt nitrate × 6H$_2$O | 563.93 | 50 | 1.84 | green |
| Potassium nitrate | 12.24 | 50/30** | 1.84 | green |
| LUDOX AS40 | 3638.04 g | 28** | 1.92 | dark green |

The LUDOX® AS40 was not added until the next day. For this reason, the solution was cooled to 30° C.

$2^{nd}$ solution: 20 l demineralized water was introduced into a 100-l sheet metal drum and then heated to 57° C. (pH-value: 5.00). The following substances were added to the demineralized water in succession:

| Substance | Quantity [g] | Temperature [° C.] | pH value | Colour of solution after addition |
|---|---|---|---|---|
| Ammonium heptamolybdate × 4H$_2$O | 5131.56 | 50 | 5.46 | colourless/greenish |
| Phosphoric acid | 280.09 | 50 | 5.42 | light green |

$3^{rd}$ solution: 2115.4 g demineralized water (20° C.) was weighed into a 10-l vessel.

| Substance | Quantity [g] | Temperature [° C.] | pH value | Colour of solution after addition |
|---|---|---|---|---|
| Nitric acid (65%) | 384.6 | 28 | — | colourless |
| Bismuth nitrate × 5H2O | 1174.90 g | 25 | — | colourless |

The $1^{st}$ solution was combined with the $2^{nd}$ solution accompanied by intensive mixing (temperature: 34° C.; pH value: 4.76). Thereafter, there was a light green suspension. The $3^{rd}$ solution was then added (temperature: 34° C.; pH value: 2.02). The suspension (ochre/yellow) was stirred for one hour. A slight gas formation was then observed.

Figure 6:
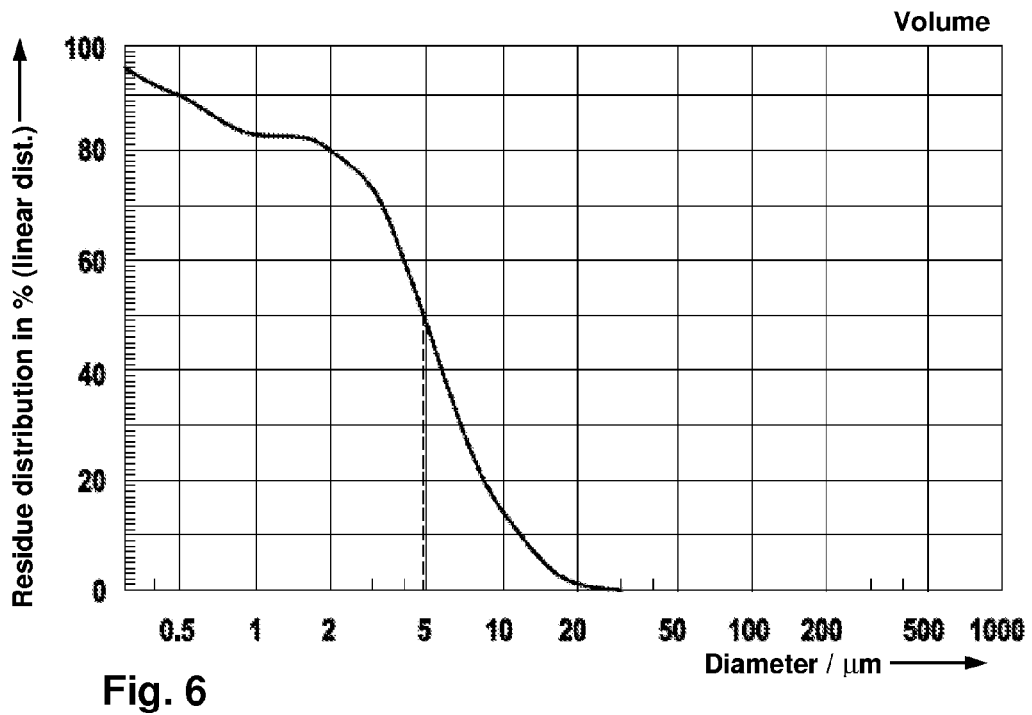
FIG. 6 shows the particle-size distribution of the suspension from Example 5.

The particle-size distribution of the suspension was determined. The results are to be found in FIG. 6.

The suspension was injected into the pulsation reactor at a dispensing rate of 20 kg/h.

The suspension was injected with the above-named parameters at 600° C. The formation of a $BiMoO_4$ phase is clear from the XRD that is not shown. The XRD spectrum is essentially identical to the XRD spectrum for Example 4 shown in FIG. 7.

2.06 kg of the powder atomized at 600° C. in the pulsation reactor and 1.07 kg of the powder atomized at 400° C. in the pulsation reactor were available for coating tests.

Example 6

Production of the Coated Catalysts

A fluidized bed coating device was used to carry out the coating.

The steatite spheres were coated with the various bismuth-molybdenum mixed oxide active materials from Examples 1 to 4 under the following conditions:

22.22 g of the material was weighed into a measuring cylinder, made into a slurry with 500 ml distilled $H_2O$. The resulting suspension was stirred intensively. 8.89 g binder was then added and the mixture stirred for 1 hour on a magnetic stirrer.

The coating of the produced suspension took place on a weighed-in sample of 80 g steatite spheres of (2-4 mm), wherein the active material charge was 20% (50 g powder per 200 g steatite spheres). The catalyst was then dried in air at 110° C.

Example 7

Determination of the Catalytic Performance Data of the Catalysts 21 g catalyst, diluted with 350 g steatite spheres (4.5 mm in diameter) to avoid hotspots, was poured into a 120-cm long reaction tube with an internal diameter of 24.8 mm to a length of 105 cm. The reaction tube was in a liquid salt bath which can be heated to temperatures of up to 500° C. In the catalyst bed there was a 3 mm protective tube with an integrated thermocouple via which the catalyst temperature over the complete catalyst combination can be displayed. To determine the catalytic performance data, 7.5 vol.-% propylene, 58 vol.-% air and nitrogen (total 100 vol.-%) were passed over the catalyst at 4500 Nl/h at most. The propylene conversion rate and the acrolein selectivity were set at an average catalyst temperature of 365° C., and the constituents of the reaction gas were analysed after leaving the reaction tube. The results of the tests with the materials obtained in Examples 1 to 4 as catalyst (produced according to Example 6) are listed in Table 1.

TABLE 1

Performance data of catalysts according to aspects of the invention and of a comparison catalyst

|  | Example 1 (comparison example) | Example 2 (according to the invention) | Example 3 (according to the invention) | Example 4 (according to the invention) |
|---|---|---|---|---|
| Propylene conversion rate | 89.5 | 91 | 93.5 | 94 |
| Acrolein selectivity | 95.3 | 96.5 | 96.5 | 96 |
| Yield | 85.2 | 87.81 | 90.3 | 90.3 |

As can be seen from Table 1, the advantages of the catalysts according to aspects of the invention are a higher yield and acrolein selectivity than with a catalyst in which the bismuth-molybdenum mixture active material was produced according to a method of the state of the art (comparison example, Example 1).

The invention claimed is:

1. A method for the production of a nanocrystalline bismuth-molybdenum mixed oxide, comprising the steps of:
   a) introducing a solution, suspension or slurry, containing a molybdenum starting compound and a bismuth starting compound, into a reaction chamber of a pulsation reactor with a carrier fluid,
   b) thermally treating a pulsating flow of the solution, suspension or slurry which contains the molybdenum starting compound and the bismuth starting compound in a treatment zone at a temperature of from 200 to 700° C., to form a nanocrystalline bismuth-molybdenum mixed oxide, and
   c) discharging the nanocrystalline bismuth-molybdenum mixed oxide obtained in step b) from the reactor.

2. The method according to claim 1, wherein the molybdenum starting compound is ammonium heptamolybdate tetrahydrate.

3. The method according to claim 1, wherein the bismuth starting compound is bismuth nitrate.

4. The method according to claim 1, wherein further metal-containing starting compounds, selected from the group consisting of nickel, iron, cobalt, manganese, zinc starting compounds, and mixtures thereof are used in the solution, suspension or slurry.

5. The method according to claim 4, wherein the further metal-containing starting compounds are selected from the group consisting of nickel, iron, zinc starting compounds and mixtures thereof.

6. The method according to claim 1, wherein the carrier fluid is a gas.

* * * * *

UNITED STATES PATENT AND TRADEMARK OFFICE
CERTIFICATE OF CORRECTION

PATENT NO. : 8,480,998 B2 Page 1 of 1
APPLICATION NO. : 12/935710
DATED : July 9, 2013
INVENTOR(S) : Hagemeyer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 310 days.

Signed and Sealed this
Eighth Day of September, 2015

Michelle K. Lee
*Director of the United States Patent and Trademark Office*